US00PP12327P2

(12) United States Plant Patent
Carruth

(10) Patent No.: US PP12,327 P2
(45) Date of Patent: Jan. 1, 2002

(54) MINIATURE ROSE PLANT NAMED 'WEKCATLART'

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 09/465,967

(22) Filed: Dec. 16, 1999

(51) Int. Cl.[7] ..... A01H 5/00
(52) U.S. Cl. ..... Plt./116
(58) Field of Search ..... Plt./116, 118, 119, Plt./120, 121, 122

(56) References Cited

U.S. PATENT DOCUMENTS

PP4,293 P * 8/1978 Schwartz ..... Plt./122

* cited by examiner

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new variety of Miniature rose suitable for garden decoration, having flowers of scarlet red coloration with a white eye zone.

1 Drawing Sheet

BACKGROUND OF THE INVENTION

This invention relates to a new and distinct variety of *Rosa hybrida* Miniature Rose. The varietal denomination of the new variety is 'WEKcatlart'. It has as its seed parent the variety known as 'POULtop' (U.S. Plant Pat. No. 9,048) and as its pollen parent the variety known as 'MACmanly' (U.S. Plant Pat. No. 6,907).

SUMMARY OF THE INVENTION

Among the features which distinguish the new variety from other presently available and known commercial rose cultivars are the following combination of characteristics: its brilliant flower color with very good color stability, its distinct white eye zone within each single petaled flower, its very long lasting flowers and its bushy, fully foliated compact plant habit that bears the flowers just above the foliage. The plant has a dwarf-like bushy compact plant growth habit, suitable for outdoor garden decoration.

Asexual reproduction of the new variety by budding as performed in Kern County and Upland, Calif., shows that the foregoing and other distinguishing characteristics come true to form and are established and transmitted through succeeding propagations. 'WEKcatlart' may be asexually propagated by cuttings, budding or grafting.

COMPARISON WITH PARENTS

The new rose may be distinguished from its seed parent, 'POULtop' by the following combination of characteristics: whereas 'WEKcatlart' bears single petaled flowers with a moderately large distinct eye zone marking, 'POULtop' bears flowers with significantly more petals (18 to 22) with a less evident eye zone marking. 'WEKcatlart' bear many prickles of varying sizes whereas 'POULtop' bears significantly less prickles of predominantly one size.

The new variety may be distinguished from its pollen parent, 'MACmanly' by the following combination of characteristics: whereas 'WEKcatlart' bears single petaled flowers of scarlet red with a white eye zone, 'MACmanly' bears flowers with significantly more petals (10 to 15) and deeper red coloration with a white eye zone. The foliage of 'MACmanly' has a very glossy finish, whereas the foliage of 'WEKcatlart' is semi-glossy to matte in finish.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specificaiton, color values are based upon The Colour Chart of The Royal Horticultural Society of London, England, except where common terms of color definition are employed.

DESCRIPTION OF THE NEW VARIETY

The following description is of 3 to 4 year old rose plants of the new cultivar grown outdoors in Upland, Calif. in the month of September. Phenotypic expression may vary with environmental, cultural and climatic conditions, as well as differences in conditions of light and soil.

FLOWER

The new variety sometimes bears its flowers singly, usually in clusters of three to four or more per stem. Flowers are borne in irregular somewhat flat to slightly rounded clusters, i.e. corymb, on strong short stems (about 6 to about 10 cm.). Outdoors, the plant blooms very abundantly and nearly continuously during the growing season. The flowers have no fragrance.

BUD

The peduncle is about 2.8 to about 4 cm. in length. It is moderately rough with many stipitate glands and some very small prickles. Peduncle color is between 144A and 146C. The side exposed to the sun is usually blushed with between 178A and 183B. The peduncle is about 0.1 to about 0.2 cm. in diameter at the widest point.

Before the calyx breaks, the bud is about 0.8 to about 1.1 cm. in diameter at the widest point, about 1.7 to about 2.2 cm. in length, and pointed to ovoid in shape. The surface of the bud bears some stipitate glands, usually with slender entire to somewhat cut foliaceous parts extending beyond the tip of the bud about ½ or more of its length. Bud color is between 144A and 146C often blushed with between 178A and 183B.

The inner surface of the sepals is covered with fine wooly tomentum; sepal margins are lined with some stipitate glands and hairs.

As the petals open (after the calyx breaks), the bud is about 0.9 to about 1.2 cm. in diameter at the widest point, about 1.9 to about 2.4 cm. in length, and pointed to ovoid in form. The color of the under surfaces of the newly opened petals is between 42A and 45A. At the point where the petal attaches, there is a moderately large zone of between 2C and 3D. The color of the upper surfaces of the newly opened petals is between 45A and 46B. At the point where the petal attaches, there is a moderately large zone of between 3C and 5C.

BLOOM

When fully open, the bloom ranges from about 4 to about 5 cm. in diameter. Petalage is single with about 5 to 6 petals and about 1 to 2 petaloids arranged irregularly. When partially open, the bloom form is very high centered to pointed, and the petals are somewhat tightly spiraled with petal edges very slightly reflexed outward. When fully open, the bloom form is more flat to slightly cupped, and the petals are somewhat flat to undulated with petal edges very slightly reflexed outward.

PETALS

The substance of the petals is very heavy and very thick with upper surfaces moderately velvety to satiny and under surfaces more shiny to satiny. The petals are nearly round to broadly obovate in shape with rounded apices. The petal margin is entire. Petals are about 1.3 to about 1.8 cm. in length and about 1.4 to about 1.8 cm. in width at the widest point.

NEWLY OPENED FLOWER

The under surface of the petals is between 42A and 46C. At the point where the petal attaches, there is a moderately large zone of between 157D and 155C. The upper surface of the petals is between 44A and 45A. At the point where the petal attaches, there is a very distinct moderately large zone of between 155B and 155D.

The general tonality of the newly opened flower is between 44A and 45A with a moderately large eyezone of between 155B and 155D.

THREE DAY OLD FLOWER

The under surface of the petals is between 45D and 43B. At the point where the petal attaches, there is a moderately large zone of near 155A. The upper surface of the petals is between 44B and 45C. At the point where the petal attaches, there is a very distinct moderately large zone of near 155B.

The general tonality of the three day old flower is between 44B and 45C with a moderately large eyezone of near 155B.

On the spent bloom, the petals usually drop off cleanly.

In September in Upland, Calif., blooms on the bush growing outdoors generally last about five or more days. Cut roses from plants grown outdoors and kept at normal indoor living temperatures generally last about five or more days.

MALE REPRODUCTIVE ORGANS

Stamens are average to many in number (average about 80) and are arranged regularly about the pistils. The filaments are irregular in length, most with anthers. Filaments are between 10A and 14C in color. The anthers are moderately large for the class and all open approximately at the same time. Anther color is near 14B when immature and near 164A at maturity. Pollen is very abundant and near 13D in color. Stamens about 0.2 to about 0.4 cm in length. The pistils are about 0.4 to about 0.6 cm. in length.

FEMALE REPRODUCTIVE ORGANS

Pistils vary in number (average about 40). The styles are somewhat uneven and loosely bunched. Stigma and style color is near between 1C and 4C. Ovaries are usually all enclosed in the calyx.

Hips on this variety when grown in Upland, Calif. are moderately globular in form, and near 28A in color when ripe. The hip surface is very smooth with somewhat thick fleshy walls. The sepals are moderately fugacious. There are approximately 5 to 8 moderately small seeds. Seeds are irregularly rounded, about 0.3 to about 0.4 cm. in diameter at the widest point and between 180A and 178C in color.

FOLIAGE

The compound leaves are usually comprised of three to five or more leaflets and are borne very abundantly. The five leaflet leaves are about 4.8 to about 6.5 cm. in length and about 3.5 to about 4.5 cm. in width at the widest point, and moderately semi-glossy to matte in finish. The five-leaflet leaves are moderately heavy in texture. The venation pattern is pinnate and the vein color is between 147B and 139B. The terminal leaflets are about 2.1 to about 2.6 cm. in length and about 1.4 to about 1.7 cm. in width at the widest point, oval to somewhat ovate in shape with acute apices and somewhat round to moderately acute bases. Their margins are usually simply serrate. The sepals are about 5 in number, about 1.2 to about 2.6 cm. in length and about 0.4 to about 0.8 cm. at the widest point. The under surface of the sepal is between 144A and 144C sometimes lightly suffused with between 178A and 183B. The upper surface of the sepal is between 148B and 191B.

The petiole is about 0.8 to about 1.1 cm. in length and less than about 0.1 cm. in diameter at the widest point. The petiolule is about 0.1 to about 0.2 cm. in length and less than about 0.1 cm. in diameter at the widest point. The petiole and petiolule color is between 144A and 144C, sometimes lightly suffused with between 178A and 183B.

The upper surface of the mature leaf is between 147A and 193A. The under surface of the mature leaf is between 148B and 191B. The upper surface of the young leaf is between 146A and 137A, sometimes lightly suffused with between 178A and 183B. The under surface of the young leaf is between 147B and 138A, often lightly suffused with between 178A and 183B.

The rachis is moderately smooth. The upper side is shallowly grooved with some stipitate glands on the edges of the grooves. The under side of the rachis is very smooth with few stipitate glands and very few small prickles.

The stipules are about 0.4 to about 0.6 cm. in length and of medium width with straight points that usually turn out an an angle of less than 45 degrees. The stipule color is between 144A and 144C, sometimes lightly suffused with between 178A and 183B.

The plant displays an above average degree of resistance to powdery mildew and rust as comapred to other commercial varieties grown under comparable conditions in Upland, Calif.

GROWTH

The plant has a dwarf-like bushy compact low to medium height growth habit (about 28 to about 42 cm. in height and spread at the widest point), with very full branching. It displays very vigorous growth. The plant usually takes between 10 to 14 days to initiate root development, depending on temperature and time of the year.

The color of the major stems is between 147C and 138B. They bear many large prickles that are about 0.6 to about 0.8 cm. in length. The large prickles are very straight and angled slightly downward with a moderately long narrow base; prickle color is between 165B and 166C. The major stem bears several small prickles of varying sizes but of similar shape and coloration.

The lateral branches are about 7.0 to about 11.0 cm. in length and about 0.2 to about 0.4 cm in diameter at the widest point. The lateral branches are variable in number. The internode is about 1.5 to about 2.1 cm in length.

The color of the branches is between 147B and 138A. They bear many large prickles that are about 0.6 to about 0.8 cm. in length. The large prickles are very straight and angled slightly downward with a moderately long narrow base; prickle color is between 180A and 178C. The major stem bears several small prickles of varying sizes but of similar shape and coloration.

The color of the new shoots is near 144A often suffused with between 178A and 183B. They bear many large prickles that are about 0.6 to about 0.8 cm. in length. The large prickles are very straight angled slightly downward with a moderately long narrow base; prickle color is between 178A and 183A. The major stem bears several small prickles of varying sizes but of similar shape and coloration.

The plant's winter hardiness and drought/heat tolerance are yet to be determined.

I claim:

1. A new and distinct Miniature rose plant of the variety substantially as described and illustrated herein.

* * * * *

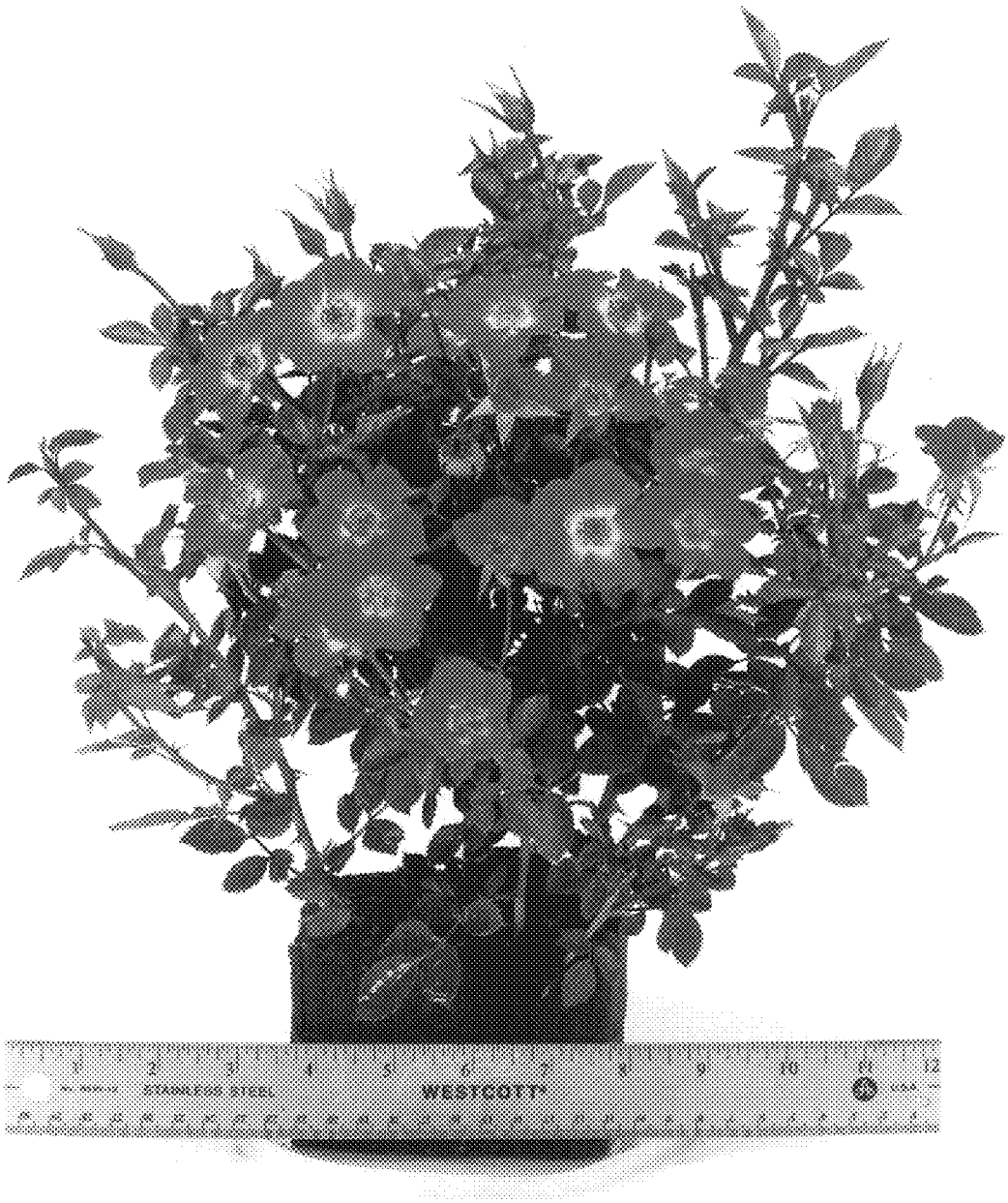
STAINLESS STEEL
WESTCOTT